United States Patent [19]

Iwasaki et al.

[11] 4,232,106
[45] Nov. 4, 1980

[54] PHOTOSENSITIVE COMPOSITIONS CONTAINING 2-HALOMETHYL-5-VINYL-1,3,4-OXADIAZOLES AS FREE RADICAL PROGENITORS

[75] Inventors: Masayuki Iwasaki; Shigeru Sato, both of Minami-ashigara; Yasuo Inoue; Akira Nagashima, both of Shizuoka, all of Japan

[73] Assignee: Fuji Photo Film Co., Ltd., Minami-ashigara, Japan

[21] Appl. No.: 961,164

[22] Filed: Nov. 16, 1978

[30] Foreign Application Priority Data

Nov. 28, 1977 [JP] Japan ................................ 52/142473

[51] Int. Cl.² .......................... G03C 1/68; G03C 1/52
[52] U.S. Cl. ..................................... 430/170; 430/920; 430/270; 430/281; 430/283; 430/285; 430/288; 430/194; 430/177; 430/179; 430/495; 430/338; 430/343; 430/339; 430/345; 430/171; 430/195; 542/458; 542/459
[58] Field of Search ..................... 96/91 R, 88, 115 P, 96/91 N, 90 R, 90 PC; 542/458, 459; 430/920, 270, 281, 283, 285, 288, 170, 194, 177, 179, 495, 338, 343, 339, 345, 171, 195

[56] References Cited

U.S. PATENT DOCUMENTS 3,708,297  1/1973  Poot et al. .......................... 96/90 R
3,954,475  5/1976  Bonham et al. ...................... 96/88

Primary Examiner—Won H. Louie, Jr.
Attorney, Agent, or Firm—Sughrue, Rothwell, Mion, Zinn and Macpeak

[57] ABSTRACT

Photosensitive compositions containing 2-halomethyl-5-vinyl-1,3,4-oxadiazole compounds represented by the following general formula (I):

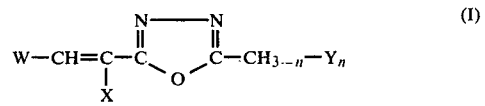

wherein W represents a substituted or unsubstituted aryl group, X represents a hydrogen atom, an alkyl group or an aryl group, Y represents a fluorine atom, a chlorine atom or a bromine atom, and n represents an integer of 1 to 3.

13 Claims, No Drawings

PHOTOSENSITIVE COMPOSITIONS CONTAINING 2-HALOMETHYL-5-VINYL-1,3,4-OXADIAZOLES AS FREE RADICAL PROGENITORS

BACKGROUND OF THE INVENTION

1. Field of the Invention

The present invention relates to photosensitive compositions containing novel compounds which generate free radicals upon exposure to light. In greater detail, it relates to a photosensitive composition containing a novel 2-halomethyl-5-vinyl-1,3,4-oxadiazole compound.

2. Discussion of the State of the Art

Compounds which decompose upon exposure to light to generate free radicals (free radical generating agents) are well known in the graphic arts. They have been widely used as photopolymerization initiators in photopolymerizable compositions, as photoactivators in free radical photographic compositions and as photo initiators for reactions catalyzed by acids formed by light. Using such free radical generating agents, various photosensitive materials useful for printing, duplicating, copying or other image formation are produced.

Organic halide compounds decompose upon exposure to light to generate halogen free radicals such as a chlorine free radical or a bromine free radical. These halogen free radicals easily abstract hydrogen extracting agents and form acids when a hydrogen donator is present. Application of such halide compounds to photopolymerization processes and free radical photographic processes have been described in *Light-Sensitive Systems* written by J. Kosar, pp. 180–181 and pp. 361–370, J. Wiley & Sons (New York, 1965).

As such compounds which generate free radicals by a function of light, carbon tetrabromide, iodoform and tribromoacetophenone are typical examples, which have been widely used heretofore. However, these free radical generating agents suffer from the drawback that they decompose only upon exposure to light in a limited wavelength range. Namely, they are sensitive to light in an ultraviolet range which is shorter than the main wavelength of the light sources generally used. As a result, these compounds have a poor free radical generating capability, because they do not have the ability of effectively utilize light of near ultraviolet range to visible range.

For the purpose of overcoming this drawback, it has been proposed to expand the photosensitive wavelength range by adding certain kinds of sensitizers. There are, for example, sensitizers such as merocyanine dyes, styryl bases and cyanine bases, disclosed in U.S. Pat. No. 3,106,466 and No. 3,121,633. Although the addition of these sensitizers expands the sensitive wavelength range of carbon tetrabromide or iodoform to the visible range, the result is still not satisfactory since it is difficult to select a sensitizer which has good compatibility with the free radical generating agents or other elements in the photosensitive composition and has high sensitivity, though selection of the sensitizer having such compatibility is necessary. Further, in those cases where system comprising a sensitizer and a free radical generating agent is incorporated with another photosensitive system, for example, in the case of a photosensitive resist forming composition in which visible images are obtained immediately upon exposing to light, the above-described sensitizers can reduce the sensitivity (the resist sensitivity) of the composition.

SUMMARY OF THE INVENTION

Accordingly, an object of the present invention is to provide photosensitive compositions which contain a free radical generating agent having good compatibility with other elements present in the photosensitive resist forming composition, having high photo-decomposition sensitivity, and which have a photosensitive wavelength range from near ultraviolet to the visible range.

Further, another object of the present invention is to provide free radical generating agents which do not reduce the sensitivity of the photosensitive resist forming composition when added thereto.

These and other objects of the present invention will become more apparent from the following description of the invention.

As the result of many studies in this field, the present inventors have discovered novel 2-halomethyl-5-vinyl-1,3,4-oxadiazole compounds represented by the following general formula (I) which are useful as free radical generating agents for attaining the above described objects:

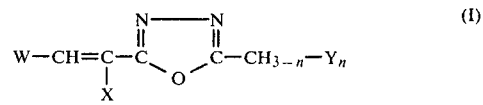

wherein W represents an aryl group which may be substituted or unsubstituted, X represents a hydrogen atom, an alkyl group or an aryl group, Y represents a fluorine atom, a chlorine atom or a bromine atom (preferably chlorine or bromine), and n represents an integer of 1 to 3 (preferably 3).

DETAILED DESCRIPTION OF THE INVENTION

W is an aryl group having 6 to 18 carbon atoms (for example, a phenyl group or naphthyl group) which may be substituted. Preferably the aryl group is a monocyclic or bicyclic aryl group. Typical examples of the substituents for the aryl group include a nitro group, a cyano group, halogen atoms, a phenyl group, lower straight, branched or cyclic alkyl groups (having 1 to 6 carbon atoms), alkoxy groups (having 1 to 6 carbon atoms), a phenoxy group and an acetoxy group. Preferably W is phenyl, alkoxyphenyl or halogenophenyl.

X is a hydrogen atom, an alkyl group having 1 to 6 carbon atoms (typical examples of which include a methyl group and a propyl group), or an aryl group having 6 to 10 carbon atoms which may be substituted (for example, a phenyl group). Typical examples of the substituents for the aryl group include a methyl group, an alkoxy group having 1 to 4 carbon atoms, a halogen atom (e.g., fluorine, chlorine, bromine) and a nitro group. Preferably X is hydrogen.

The above-described 1,3,4-oxadiazole compounds yield a free radical upon exposure to electromagnetic radiation having wavelengths of about 300 to about 500 nm. For this reason, these compounds are useful as a photoreaction initiators for photosensitive compositions and elements. Thus, they can be incorporated in photopolymerizable compositions and printing compositions useful for producing printing plates, such as lithographic plates, relief plates or gravure plates, etc., photo-resists and photographic elements, and photosensitive resist forming compositions with which visible images are obtained upon exposure to light.

The novel 2-halomethyl-5-vinyl-1,3,4-oxadiazoles can be advantageously synthesized by a series of reactions represented by the following equations.

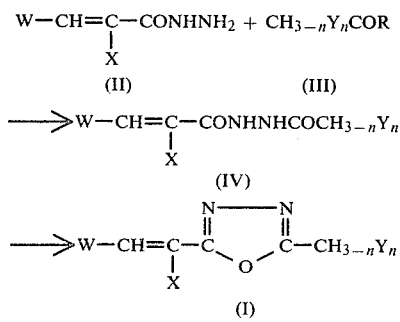

wherein W, X, Y and n have the same definition as in general formula (I), and R represents a trichloromethyl group, $-O-CO-CH_{3-n}Y_n$, a fluorine atom, a chlorine atom or a bromine atom.

Among acrylic acid hydrazide derivatives represented by the general formula (II) used for production of the compounds of the present invention in accordance with the above equations, preferred examples include cinnamic acid hydrazide, p-nitrocinnamic acid hydrazide, p-cyanocinnamic acid hydrazide, 2,4-dichlorocinnamic acid hydrazide, p-chlorocinnamic acid hydrazide, p-methylcinnamic acid hydrazide, p-methoxycinnamic acid hydrazide, m-methoxycinnamic acid hydrazide, o-methoxycinnamic acid hydrazide, p-n-butoxycinnamic acid hydrazide, 3,4-methylenedioxycinnamic acid hydrazide, naphthylacrylic acid hydrazide, α-methylcinnamic acid hydrazide and α-phenylcinnamic acid hydrazide, etc. Synthesis of these acrylic acid hydrazide derivatives can be carried out according to processes described in *Acta Chem. Scand.* 9 1498 (1955) written by W. O. Godfredsen & S. Vangedal and *Bull. Chem. Soc. Jap.*, 41 (10) 2521 (1968) written by S. Harada & H. Kondo.

Among compounds represented by the general formula (III) used for production of the compounds of the present invention, preferred examples include hexachloroacetone, hexabromoacetone, trichloroacetic acid anhydride, dichloroacetic acid anhydride, monochloroacetic acid anhydride, tribromoacetic acid anhydride, dibromoacetic acid anhydride, monobromoacetic acid anhydride, trichloroacetyl chloride, dichloroacetyl chloride, monochloroacetyl chloride, tribromoacetyl bromide, dibromoacetyl bromide, monobromoacetyl chloride and monobromoacetyl bromide, etc.

Production of the compounds represented by the general formula (IV) from the compounds represented by the general formulae (II) and (III) can be carried out by the following processes. For example: (1) a process of stirring an acrylic acid hydrazide derivative with a slightly excess amount of a hexachloroacetone or a hexabromoacetone in a solvent such as acetonitrile at from room temperature to a refluxing temperature, (2) a process of stirring an acrylic acid hydrazide derivative with an equimolar amount of haloacetic acid anhydride at a room temperature, and (3) a process of stirring 2 moles of an acrylic acid hydrazine derivative with 1 mole of a haloacetyl halide using dioxane or tetrahydrofuran as a solvent at a room temperature.

Production of 1,3,4-oxadiazoles from corresponding compounds represented by the general formula (IV) is carried out according to the process described in *J. Heterocyclic Chem.*, 7 (3) 511 (1970) written by M. P. Hutt, E. F. Elslager and L. M. Werbel.

Compounds having the structure shown in Table 1 are particularly advantageous as the free radical generating agent used in the present invention.

TABLE 1

Examples of Free Radical Generating Agent

Compound No. 1

![Structure: phenyl-CH=CH-C(=N-N=)C-CCl₃ oxadiazole]

Compound No. 2

![O₂N-phenyl-CH=CH-oxadiazole-CCl₃]

Compound No. 3

![NC-phenyl-CH=CH-oxadiazole-CCl₃]

Compound No. 4

![Cl-phenyl(Cl)-CH=CH-oxadiazole-CCl₃]

Compound No. 5

![-Cl-phenyl-CH=CH-oxadiazole-CCl₃]

Compound No. 6

![CH₃-phenyl-CH=CH-oxadiazole-CCl₃]

Compound No. 7

![CH₃O-phenyl-CH=CH-oxadiazole-CCl₃]

Compound No. 8

![phenyl(CH₃O)-CH=CH-oxadiazole-CCl₃]

Compound No. 9

![phenyl(OCH₃)-CH=CH-oxadiazole-CCl₃]

Compound No. 10

![n-C₄H₉O-phenyl-CH=CH-oxadiazole-CCl₃]

Compound No. 11

![methylenedioxyphenyl-CH=CH-oxadiazole-CCl₃]

TABLE 1-continued

Examples of Free Radical Generating Agent

Compound No. 12

Compound No. 13

Compound No. 14

Compound No. 15

Compound No. 16

Compound No. 17

The compounds represented by the general formula (I) in the present invention are essentially different in structure from vinyl-halomethyl-s-triazine compounds described in U.S. Pat. No. 3,954,475 and No. 3,987,037 by J. A. Bonham, et al.

Namely, the conjugated bond between the halomethyl group and the aromatic ring in the present invention is represented by the following formula:

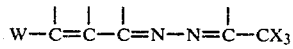

while that in the compounds proposed by Bonham et al is represented by the following formulae.

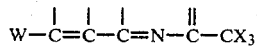

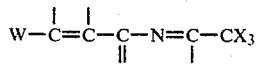

Although the compounds of the present invention are similar to the compounds proposed by Bonham et al from the standpoint that the halomethyl group is linked to a light absorbing group, the compounds of the present invention cannot be analogized to the compound proposed by Bonham et al, because the following compounds, for example, have hardly any free radical generating capability upon exposure to light.

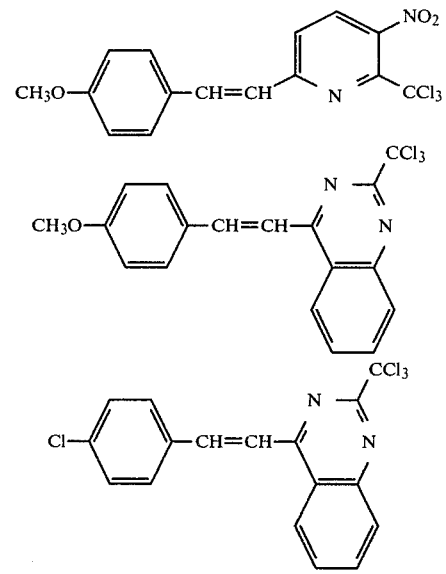

Furthermore, when using the compounds proposed by Bonham et al in a photosensitive resist forming composition which forms visible images upon exposure to light, they reduce the resist formation sensitivity of the composition. On the other hand, the compounds of the present invention do not so reduce the resist formation sensitivity of the composition, though the explanation for this is not clear. In forming resist images on a base plate, it is a great advantage in this field of art, in which working efficiency is regarded as important, that the photosensitive resist forming compositions have high sensitivity.

The compounds proposed by Bonham et al are synthesized with using methyl trihalomethyl-s-triazines as intermediates. The methyl trihalomethyl-s-triazines are synthesized generally with using haloacetonitriles as a starting material. Haloacetonitriles are generally very toxic. As a result, sufficient consideration for sanitation is required for handling at the production site. On the other hand, toxic compounds are not used to produce the compounds of the present invention.

The free radical generating agents of the present invention are particularly useful in photoresist compositions which form visible images upon exposure to light without development and used for producing lithographic printing plates, IC circuits or photomasks. In such photosensitive resist compositions, since visible images are obtained directly by only exposing the resist to light, it becomes possible under a yellow safety lamp to check whether the plates are exposed or not, for example, when operation is interrupted in the step of exposing many printing plates at the same time.

Similarly, in the situation in which one large plate is exposed to light many times such as in so-called photo composing, step and repeat printing down process for making lithographic printing plates, workers can ascertain immediately what part has been exposed.

The photosensitive resist forming compositions which form visible images immediately upon exposure to light, in which the free radical generating agents of the present invention can be used advantageously, are generally composed of (i) a photosensitive resist forming composition, (ii) a free radical generating agent and (iii) a color changing agent as essential components and, if necessary, one or more of plasticizers, binders, dyes which are not color changing agents, pigments, antifogging agents and sensitizers for the photosensitive resist forming composition, etc. The term "photosensitive resist forming compositions" as used in this specification covers both the use of the compound per se, e.g., the diazo compound, as well as the use of the compound in a binder.

The photosensitive resist forming composition may be a compound the physical properties of which (such as solubility, tackiness or adhesive property to base plates, etc.) change upon exposure to light. Examples of these compounds include photosensitive diazo compounds, photosensitive azide compounds, compounds having an ethylenically unsaturated double bond and compounds which catalytically react with the acids formed upon exposure to light.

As preferred photosensitive diazo compounds, there are compounds having two or more diazo groups in one molecule, such as a salt of the condensation products of p-diazodiphenylamine with formaldehyde. For example, the phenyl salt, the fluorocaprate salt and sulfonates thereof such as the triisopropylnaphthalene sulfonate salt, the 4,4'-biphenyldisulfonate salt, the 5-nitro-o-toluenesulfonate salt, the 5-sulfosalicylate salt, the 2,5-dimethylbenzenesulfonate salt, the 2-nitrobenzenesulfonate salt, the 3-chlorobenzenesulfonate salt, the 3-bromobenzenesulfonate salt, the 2-chloro-5-nitrobenzenesulfonate salt, the 2-fluorocaprylnaphthalenesulfonate salt, the 1-naphthol-5-sulfonate salt, the 2-methoxy-4-hydroxy-5-benzoylbenzenesulfonate salt or the p-toluenesulfonate salt, etc. As other preferred diazo compounds, there are the condensation products of 2,5-dimethoxy-4-p-tolylmercaptobenzene diazonium salts with formaldehyde and condensation products of 2,5-dimethoxy-4-morpholinobenzene diazonium salts with formaldehyde or acetaldehyde, etc.

Further, examples of useful diazo compounds include the compounds described in U.S. Pat. No. 2,649,373.

It is preferred to use the thus diazo compound in a combination with a high molecular (polymeric) binder. Many high molecular binders are known. Preferred examples of the high molecular binders which can be used in the present invention include schellac as disclosed in British Pat. No. 1,350,521, a polymer having a hydroxyethylacrylate unit or a hydroxyethylmethacrylate unit as a main repeating unit as disclosed in British Pat. No. 1,460,978 and No. 1,505,739, a polyamide resin as disclosed in U.S. Pat. No. 3,751,257, a phenol resin and a polyvinyl acetal such as a polyvinylformal resin and a polyvinyl butyral resin as disclosed in British Pat. No. 1,074,392, a linear polyurethane resin as disclosed in U.S. Pat. No. 3,660,097, a polyvinylalcohol phthalated resin, an epoxy resin prepared by condensation of bisphenol A and epichlorohydrin, a polymer having an amino group such as polyaminostyrene and polyalkyl amino (meth)acrylate, and celluloses such as cellulose acetate, cellulose alkyl ether and cellulose acetate phthalate, etc.

They become insoluble upon exposure to actinic radiation, as the diazo groups decompose.

On the other hand, it is possible to use photosensitive diazo compounds which become alkali soluble upon application of actinic radiation. They are compounds having at least one o-quinonediazide group in the molecule, and sulfonic acid ester or sulfonic acid amides of o-quinonediazides are particularly preferred. A number of such compounds are already known. For example, there are the compounds described in U.S. Pat. Nos. 3,046,110, 3,046,111, 3,046,115, 3,046,119, 3,046,120, 3,046,121, 3,046,122, 3,130,047, 3,130,048, 3,188,210, 3,184,310, 3,130,048, 3,102,809, 3,148,983, 3,454,400 and 3,859,099, etc.

The o-quinonediazide compound is preferably used together with an alkali-soluble resin which is used as binder. Preferred examples of the alkali-soluble resin include a novolak type phenol resin such as phenol formaldehyde resin, o-cresol formaldehyde resin, m-cresol formaldehyde resin and the like. It is more preferred to use the phenol resin above together with a condensation product of a phenol or cresol, which is substituted with an alkyl group having 3 to 8 carbon atoms, and a formaldehyde, for example, t-butyl phenol formaldehyde resin as disclosed in Japanese patent application (OPI) No. 125806/75 (The term "OPI" as used herein refers to a "published unexamined Japanese patent application"). The amount of the alkali-soluble resin used in the present invention is about 50 to about 85 wt%, preferably 60 to 80 wt%, based on the total weight of the composition comprising the photosensitive layer of the present invention.

Preferred photosensitive azide compounds are aromatic azide compounds wherein the azide group is linked to the aromatic ring directly or through a carbonyl or a sulfonyl group. Upon exposure to light as the azide group decomposes to yield a nitrene which causes various reactions and thereby become insoluble. As preferred aromatic azide compounds, there are compounds containing one or more groups such as azidophenyl groups, azidostyryl groups, azidobenzal groups, azidobenzoyl groups or azidocinnamoyl groups. Examples of which include 4,4'-diazidochalcone, 4-azido-4'-(4-azidobenzoylethoxy)chalcone, N,N-bis-p-azidobenzal-p-phenylenediamine, 1,2,6-tri(4'-azidobenzoxy)hexane, 2-azido-3-chlorobenzoquinone, 2,4-diazido-4'-ethoxyazobenzene, 2,6-di(4'-azidobenzal)-4-methylcyclohexanone, 4,4'-diazidobenzophenone, 2,5-diazido-3,6-dichlorobenzoquinone, 2,5-bis(4-azidostyryl)-1,3,4-oxidiazole, 2-(4-azidocinnamoyl)thiophene, 2,5-di(4'-azidobenzal)cyclohexanone, 4,4'-diazidodiphenylmethane, 1-(4-azidophenyl)-5-furyl-2-penta-2,4-diene-1-one, 1-(4-azidophenyl)-5-(4-methoxyphenyl)-penta-1,4-diene-3-one, 1-(4-azidophenyl)-3-(1-naphthyl)propene-1-one, 1-(4-azidophenyl)-3-(4-dimethylaminophenyl)propane-1-one, 1-(4-azidophenyl)-5-phenyl-1,4-pentadiene-3-one, 1-(4-azidophenyl)-3-(4-nitrophenyl)-2-propene-1-one, 1-(4-azidophenyl)-3-(2-furyl)-2-propene-1-one, 1,2,6-tri(4'-azidobenzoxy)hexane, 2,6-bis(4-azidobenzylidine-p-t-butyl)cyclohexanone, 4,4'-diazidodibenzalacetone, 4,4'-diazidostilbene-2,2'-disulfonic acid, 4'-azidobenzalacetophenone-2-sulfonic acid, 4,4'-diazido-stilbene-α-carboxylic acid, di(4-azido-2'-hydroxybenzal)acetone-2-sulfonic acid, 4-azidobenzalacetopnenone-2-sulfonic acid, 2-azido-1,4-dibenzenesulfonylaminonaphthalene and 4,4'-diazidostilbene-2,2'-disulfonic acid anilide, etc.

In addition to these low molecular weight aromatic azide compounds, azide containing polymers described in Japanese Pat. Nos. 9047/69, 31837/69, 9613/70, 24915/70 and 25713/70 are preferred to use. These azide compounds are preferably used together with a water-soluble or alkali-soluble high molecular compound which is used as a binder; for example, the compounds disclosed in British Pat. No. 1,235,281 and No. 1,495,861.

Preferred compounds having ethylenically unsaturated bonds are polymers capable of cross-linking by a photodimerization reaction of the ethylene bond and vinyl monomers which form insoluble polymers by photopolymerization in the presence of a photopolymerization initiators.

As the polymers having ethylenically unsaturated bonds which become insoluble upon photo-dimerization, there are polyesters, polyamides and polycarbonates having

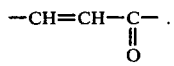

Examples of such polymers include photosensitive polymers containing photosensitive groups in the polymer main chain as described in U.S. Pat. No. 3,030,208 and No. 3,707,373, for example, photosensitive polyesters composed of p-phenylene diacrylic acid and diols; photosensitive polymers described in U.S. Pat. No. 2,956,878 and No. 3,173,787, for example, photosensitive polyesters derived from 2-properidene malonic acid compounds such as cinnamylidene malonic acid, etc., and difunctional glycols; and photosensitive polymers described in U.S. Pat. Nos. 2,690,966, 2,752,372 and 2,732,301, for example, cinnamic acid esters of hydroxyl group containing polymers such as polyvinyl alcohol, starch, cellulose and the like.

As the vinyl monomers which form insoluble polymers by photopolymerization in the presence of a photopolymerization initiator, there are compounds having at least two terminal vinyl groups.

Examples of vinyl monomers include acrylic acid or methacrylic acid esters of polyols described in Japanese Pat. Nos. 5093/60, 14719/60 and 28727/69 such as diethylene glycol diacrylate or dimethacrylate, triethylene glycol diacrylate or dimethacrylate, pentaerythritol triacrylate or trimethacrylate and trimethylolpropane triacrylate or trimethacrylate, bisacrylamides and bismethacrylamides such as ethylenebisacrylamide or methacrylamide and urethane group containing unsaturated monomers such as reaction products of diol monoacrylates and diol monomethacrylates and diisocyanate, for example, di(2'-methacryloxyethyl)-2,4-tolylenediurethane or di(2'-acryloxyethyl)trimethylenediurethane, etc. Details of the composition containing the vinyl monomers are disclosed in U.S. Pat. No. 4,072,528 and No. 4,072,527.

As the color changing agents used for production of the photosensitive resist forming compositions capable of obtaining visible images directly by exposure to light alone, there are two types of compounds: Namely, one is colorless compound which changes to a colored state by the action of a light decomposition product of the free radical generating agent and the other has an inherent color which discolors or fades by said action.

As typical color changing agents of the former type, there are arylamines. As the arylamines suitable for such a purpose, there are not only mere arylamines such as primary and secondary aromatic amines but also the so-called leuco dyes, examples of which include the following compounds.

Diphenylamine, dibenzylaniline, triphenylamine, diethylaniline, diphenyl-p-phenylenediamine, p-toluidine, 4,4'-biphenyldiamine, o-chloroaniline, o-bromoaniline, 4-chloro-o-phenylenediamine, o-bromo-N,N-dimethylaniline, 1,2,3-triphenylguanidine, naphthylamine, diaminodiphenylmethane, aniline, 2,5-dichloroaniline, N-methyl-diphenylamine, o-toluidine, p,p'-tetramethyldiaminodiphenyl methane, N,N-dimethyl-p-phenylenediamine, 1,2-dianilinoethylene, p,p'p''-hexamethyl triaminotriphenyl methane, p,p'-tetramethyldiaminodiphenyl methylimine, p,p',p''-triamino-o-methyltriphenylmethane, p,p',p''-triaminotriphenyl carbinol, p,p'-tetramethylaminodiphenyl-4-anilino-naphthyl methane, p,p',p''-triaminotriphenyl methane and p,p',p''-hexapropyltriaminotriphenyl methane.

As the color changing agents having an inherent color which discolors or fades by the light decomposition product of the free radical generating agent, various dyes such as diphenylmethane type, triphenylmethane type, thiazine type, oxazine type, xanthene type, anthraquinone type, iminonaphthoquinone type and azomethine type dyes are effectively used. Examples of such dyes include the following materials. Brilliant Green, Eosine, Ethyl Violet, Erythrocin B, Methyl Green, Crystal Violet, basic Fuchsine, phenolphthalein, 1,3-diphenyltriazine, Alizarin Red S, Thymolphthalein, Methyl Violet 2B, Quinaldine Red, Rose Bengale, Metanil Yellow, Thymolsulfophthalin, Xylenol Blue, Methyl Orange, Orange IV, diphenylthiocarbazone, 2,7-dichlorofluorescein, Paramethyl Red, Congo Red, Benzopurpurin 4B, α-Naphthyl Red, Nile Blue, Phenacetalin, Methyl Violet, Malachite Green, Parafuchsine, Oil Blue #603 (produced by Orient Kagaku Kogyo Co.), Oil Pink #312 (produced by Orient Kagaku Kogyo Co.), Oil Red 5B (produced by Orient Kagaku Kogyo Co.), Oil Scarlet #308 (produced by Orient Kagaku Kogyo Co.), Oil Red OG (produced by Orient Kagaku Kogyo Co.), Oil Red RR (produced by Orient Kagaku Kogyo Co.), Oil Green #502 (produced by Orient Kagaku Kogyo Co.), Spiron Red BEH special (produced by Hodogaya Chemical Co.), m-Cresol purple, Cresol Red, Rhodamine B, Rhodamine 6G, Fast Acid Violet R, Sulfo Rhodamine B, Auramine, 4-p-diethylaminophenyliminonaphthoquinone, 2-carboxyanilino-4-p-diethylaminophenyliminonaphthoquinone, 2-carbostearylamino-4-p-dihydroxyethylaminophenylimino naphthoquinone, p-methoxybenzoyl-p'-diethylamino-o'-methylphenylimino-acetanilide, cyano-p-diethylaminophenylimino-acetanilide, 1-phenyl-3-methyl-4-p-diethylaminophenylimino-5-pyrazolone and 1-β-naphthyl-4-p-diethylaminophenylimino-5-pyrazolone.

In the photosensitive compositions of the present invention, though the light activating agents are stable with the lapse of time, leuco triphenylmethane dyes used as the color changing agents are generally easily oxidized. Therefore, it is effective to incorporate a stabilizer when such dyes are used. As preferred stabilizers for this purpose, there are amines described in U.S. Pat. No. 3,042,575, zinc oxide, phenols, sulfur compounds described in U.S. Pat. No. 3,042,516, alkali metal iodides described in U.S. Pat. No. 3,042,518, organic acids, organic acid anhydrides described in U.S. Pat. No. 3,082,086, and triaryl compounds of antimony, arsenic, bismuth and phosphorus described in U.S. Pat. No. 3,377,167.

The photosensitive compositions of the present invention are used by dissolving the above-described components in a solvent and application to a suitable support by a known method. In the following table, preferred ratios and particularly preferred ratios of each component in a photopolymerizable composition in accordance with the invention are shown as parts by weight based on 100 parts by weight of the photosensitive resist forming compound or composition.

|  | Preferred (parts by weight) | Particularly Preferred (parts by weight) |
| --- | --- | --- |
| Free radical generating agent of the present invention | 0.01–100 | 0.1–50 |
| Color changing agent | 0.1–50 | 1–10 |
| Plasticizer | 0–1,000 | 0–500 |
| Binder | 0–5,000 | 0–1,000 |
| Dye or pigment other than the color changing agent | 0–100 | 0–50 |
| Anti-fogging agent | 0–50 | 0–20 |
| Sensitizer for photosensitive resist forming compound | 0–50 | 0–20 |

As the solvent used for applying the photosensitive compositions of the present invention to a support, there may be used ethylene dichloride, cyclohexanone, methyl ethyl ketone, methyl cellosolve acetate, monochlorobenzene, toluene and ethyl acetate.

These solvents are used alone or in admixture. In cases of producing photosensitive lithographic printing plates, a preferred amount of photopolymerizable composition is generally in a range of 0.1 to 10.0 g/m$^2$ as the solid content and, particularly, 0.5 to 5.0 g/m$^2$.

The photosensitive compositions of the present invention are suitable as the sensitive layer of photosensitive lithographic printing plates. As supports suitable for the photosensitive lithographic printing plates, there are aluminium plates processed to give them a hydrophilic property, for example, aluminium plates treated with an aqueous alkali metal silicate solution, anodized aluminium plates, grained aluminium plates or silica electrodeposited aluminium plates, zinc plates, stainless steel plates, chromium treated copper plates, plastic films processed so as to have a hydrophilic property and paper.

In the case of using photosensitive compositions of the present invention for producing correction plates for printing, films for overhead projectors or films for intermediate originals, suitable supports include transparent films such as polyethylene terephthalate films or cellulose triacetate films, etc., and those plastic films the surface of which has been chemically or physically matted.

When using the photosensitive compositions of the present invention for producing films for photomasks, the preferred supports include polyethylene terephthalate films on which aluminium, aluminium alloy or chromium has been deposited by evaporation and polyethylene terephthalate films having a colored layer.

Further, in cases of using the compositions of the present invention as a photoresist, copper plates, copper plated plates, stainless steel plates and glass plates, etc., can be used as the support.

It is a surprising fact that the free radical generating agents according to the present invention decompose in the photosensitive resist forming composition containing various photosensitive resist forming compounds to efficiently and immediately change the color of a coexistent color changing agent when subjected to the action of light. Consequently, distinct boundaries are obtained between the exposed potions and unexposed portions, which can be observed as visible images having good contrast.

Further, since various kinds of color changing agents can be used, a suitable color changing agent can be selected when various additives were added in order to improve the properties of the photosensitive compositions.

Further, when the free radical generating agents used in the present invention are used in sensitive materials to which photosensitivity was previously provided, such as a photosensitive printing plate, etc., their storage life is improved because the free radical generating agents are stable to the lapse of time.

Moreover, the free radical generating agents according to the present invention are effective even when added in a small amount, because they have a very wide spectral sensitivity range which is not interrupted or shielded by coexisting photosensitive resist forming compounds.

Further, since the free radical generating agents according to the present invention do not hinder the photo decomposition of the photosensitive resist forming compounds, they do not reduce the photosensitivity (resist sensitivity) of the photosensitive resist forming compositions. Moreover, since the free radical generating agents according to the present invention are effective in small amounts, they do not cause deterioration of physical properties of resist images obtained on the photosensitive resist forming composition by image exposure and development thereof. For example, when the photosensitive resist forming composition of the present invention is used as a sensitive layer of a photosensitive lithographic printing plate, properties of the resultant printing plate, such as developability, oil-sensitivity, printing stains or printing endurance, etc., are the same as those when the free radical generating agent is not added.

The present invention will become more clear by reference to the following examples wherein all parts, percents, ratios, etc., are by weight unless otherwise indicated.

EXAMPLE 1

Process for Producing 2-Trichloromethyl-5-(p-methoxystyryl)-1,3,4-oxadiazole 17.8 g of p-methoxycinnamic acid and 13.9 g of p-nitrophenol were refluxed by heating for 1 hour in 50 ml of thionylchloride and 50 ml of benzene. After the excess thionylchloride and benzene were distilled off, the resultant solid was washed with water and dried. Thus, a stoichiometric amount of p-methoxycinnamic acid p′-nitrophenyl ester was obtained.

18.0 g of p-methoxycinnamic acid p′-nitrophenyl ester was added to a solution of 11.4 g of 80% hydrazine hydrate in 75 ml of methanol, and the solution was refluxed for 30 minutes with heating. After cooling the reaction solution by allowing it to stand, 6.3 g of triethylamine was added thereto and the solution was added to 400 ml of water. Thus, 7.9 g of p-methoxycinnamic acid hydrazide was obtained as colorless crystal.

19.2 g of p-methoxycinnamic acid hydrazide was added to a solution of 29.2 g of hexachloroacetone in 100 ml of acetonitrile, and the solution was refluxed for 20 minutes with heating. When the reaction solution was cooled, 30.1 g of N-p-methoxycinnamoyl-N′-trichloroacetyl hydrazide was removed as a colorless crystal.

4 g of N-p-methoxycinnamoyl-N'-trichloroacetyl hydrazide and 40 ml of phosphorus oxychloride were refluxed for 3 hours with heating. The mixture was added to 200 g of ice water. The resulting precipitate was recrystallized from methanol to obtain 2.5 g of 2-trichloromethyl-5-(p-methoxystyryl)-1,3,4-oxidiazole (melting point: 140.5°–141.5° C.).

EXAMPLE 2

Process for Producing 2-Trichloromethyl-5-(3',4'-methylenedioxystyryl)-1,3,4-oxadiazole The above described compound was obtained in the same manner as in Example 1 using 3,4-methylenedioxy cinnamic acid in place of p-methoxycinnamic acid. Melting point: 156° to 158° C.

EXAMPLE 3

Process for Producing 2-Chloromethyl-5-(p-methoxystyryl)-1,3,4-oxadiazole 1.9 g of the intermediate: p-methoxycinnamic acid hydrazide obtained in Example 1 was added to a mixture of 1.7 g of monochloroacetic acid anhydride and 15 ml of acetic acid, which was stirred at a room temperature for 30 minutes. After dilution with water, the resulting precipitate was recrystallized from a solvent mixture of methanol and water to obtain 0.8 g of N-p-methoxycinnamoyl-N'-chloroacetyl hydrazide.

0.8 of N-p-methoxycinnamoyl-N'-chloroacetyl hydrazide and 10 ml of phosphorus oxychloride were refluxed for 1 hour with heating, and the reaction solution was diluted with ice water. The resulting precipitate was recrystallized from ethanol to yield 0.4 g of 2-chloromethyl-5-(p-methoxystyryl)-1,3,4-oxadiazole (melting point: 139°–141° C.).

EXAMPLE 4

Onto an aluminium plate (I) having a thickness of 0.15 mm the surfaces of which had been grained, the following photosensitive solutions were applied by a whirler and dried at 100° C. for 2 minutes to produce photosensitive lithographic printing plates.

| | |
|---|---|
| Esterified Product of Naphthoquinone-(1,2)diazido(2)-5-sulfonylchloride and Pyrogallol Acetone Resin (prepared as in Example 1 of U.S. Pat. 3,635,709) | 0.75 g |
| Cresol Novolak Resin | 2.1 g |
| Tetrahydrophthalic Acid Anhydride | 0.15 g |
| Crystal Violet | 0.02 g |
| The Free Radical Generating Agent (in Table 2) | 0.02 g 0.03 g |
| Ethylene Dichloride | 18 g |
| Methyl Cellosolve | 12 g |

The application amount after drying as 2.2 g/m².

After the photosensitive lithographic printing plates were exposed to light at a distance of 70 cm by a carbon arc lamp of 30 amperes, they were developed at 25° C. for 60 seconds using an aqueous 5 wt% sodium silicate (molar ratio of $SiO_2/Na_2O$: 1.74) solution, and the sensitivity was measured. In this case, the optimum exposure time was taken as the time at which 5 steps of a gray scale having an optical density difference of 0.15 became completely clear.

Optical densities of the exposed portion and the unexposed portion on the sensitive layer after a time were measured using a Macbeth reflection densitometer.

Further, the above-described measurement was repeated after the photosensitive lithographic printing plates were subjected to a compulsory lapse of time. The compulsory lapse of time was carried out at 45° C. of the temperature, 75% humidity, for 7 days.

The images obtained upon exposure to light became clearer the difference (ΔD) between the density of exposed portion and the unexposed portion increased.

TABLE 2

Properties of Photosensitive Lithographic Printing Plates and Optical Density of Sensitive layer (D)

| Sample No. | Free Radical Generating Agent | Optimum Exposure Time (resist sensitivity) (seconds) | After Lapse of 1 Day after Application | | | After Compulsory Lapse of Time (45° C. 75%, for 7 days) | | |
|---|---|---|---|---|---|---|---|---|
| | | | Unexposed Portion | Exposed Portion | ΔD | Unexposed Portion | Exposed Portion | ΔD |
| 1. Comparison | None | 65 | 0.89 | 0.89 | 0.00 | 0.89 | 0.89 | 0.00 |
| 2. Invention | Compound No. 7 | 68 | 0.89 | 0.75 | 0.14 | 0.89 | 0.76 | 0.13 |
| 3. Comparison | 2,4-Bis(trichloromethyl)-6-(p-methoxystyrly)-s-triazine | 75 | 0.87 | 0.71 | 0.16 | 0.86 | 0.72 | 0.14 |
| 4. Comparison | Naphthoquinone-1,2-diazido-(2)-4-sulfonyl chloride | 66 | 0.88 | 0.78 | 0.10 | 0.87 | 0.82 | 0.05 |
| 5. Comparison | 2-Trichloromethyl-3-nitro-6-(p-methoxystyryl)pyridine | 68 | 0.89 | 0.89 | 0.00 | 0.89 | 0.89 | 0.00 |
| 6. Comparison | 2-Trichloromethyl-4-(p-methoxystryl)-quinazoline | 69 | 0.88 | 0.88 | 0.00 | 0.88 | 0.88 | 0.00 |

In Table 2, free radical generating agent No. 7 of the present invention exhibits excellent stability with time in comparison to the prior art naphthoquinone-1,2-diazido(2)-4-sulfonylchloride. Further, though the free radical generating agent No. 7 of the present invention has excellent stability with time similar to 2,4-bis(trichloromethyl)-6-p-methoxystyryl-s-triazine, the latter is inferior in that the resist sensitivity is reduced. Further, 2-trichloromethyl-3-nitro-6-(p-methoxystyryl)pyridine and 2-trichloromethyl-4-(p-methoxystyryl)quinazoline do not have the ability to change the density in the exposed portion of the resist upon exposure.

EXAMPLE 5

Process for Producing Positive Type Photosensitive Lithographic Printing Plate

Onto an aluminium plate (II) having a thickness of 0.24 mm which had been subjected to anodic oxidation after the surfaces had been grained, the following photosensitive solution was applied and dried at 100° C. for 2 minutes.

| | |
|---|---|
| Esterified Product of Naphthoquinone-(1,2)-diazido-(2)-5-sulfonyl Chloride and Cresol Novolak Resin | 0.75 g |
| Cresol Novolak Resin | 2.10 g |
| Tetrahydrophthalic Anhydride | 0.15 g |
| Compound No. 7 | 0.02 g |
| Crystal Violet | 0.01 g |
| Oil Blue #603 (produced by Orient Kagaku Kogyo Co.) | 0.01 g |
| Ethylene Dichloride | 18 g |
| Methyl Cellosolve Acetate | 12 g |

The application amount after drying was 2.2 gm/m². Clear print-out images could be obtained on this photosensitive lithographic printing plate by image exposure without development. Since the exposed portions faded and the unexposed portions maintained their original density, details of the images could be descerned under a safety lamp.

EXAMPLE 6

Process for Producing Positive Type Photosensitive Lithographic Printing Plate

Onto the aluminium plate (II) used in Example 5, the following photosensitive solution was applied in a dry amount of 2.0 g/m² to obtain a photosensitive lithographic printing plate.

| | |
|---|---|
| Esterified Product of Naphthoquinone-(1,2)-diazido-(2)-5-sulfonyl Chloride and Poly-p-hydroxystyrene (molecular weight: 7,000) | 0.70 g |
| Cresol Novolak Resin | 2.25 g |
| p-tert-Butylphenol Novolak Resin | 0.05 g |
| Tetrahydrophthalic Acid Anhydride | 0.15 g |
| Compound No. 11 | 0.02 g |
| Oil Blue #603 | 0.02 g |
| Tetrahydrofuran | 18 g |
| Methyl Cellosolve Acetate | 12 g |

When this plate was subjected to imagewise exposure, clear print-out images were obtained without carrying out development.

EXAMPLE 7

Process for Producing Positive Type Photosensitive Lithographic Printing Plate

Onto the aluminium plate (II) used in Example 5, the following photosensitive solution was applied in a dry amount of 2.0 g/m² to obtain a photosensitive lithographic printing plate. When this plate was subjected to imagewise exposure, clear print-out images were obtained without carrying out development.

| | |
|---|---|
| Esterified Product of Naphthoquinone-(1,2)-diazido-(2)-5-sulfonyl Chloride and Pyrogallolacetone Resin (used in Example 4) | 0.75 g |
| Cresol Novolak Resin | 2.10 g |
| p-tert-Butylphenol-Novolak Resin | 0.05 g |
| Tetrahydrophthalic Acid Anhydride | 0.15 g |
| Thymol Blue | 0.02 g |
| Compound No. 7 | 0.02 g |
| Ethylene Dichloride | 18 g |
| Methyl Cellosolve Acetate | 12 g |

EXAMPLE 8

Process for Producing Negative Type Lithographic Printing Plate

Onto an uncoated aluminium plate (I) used in Example 4, the following photosensitive solution was applied with a whirler. Drying was carried out at 100° C. for 2 minutes.

| | |
|---|---|
| The p-Toluenesulfonate of Condensation Product of p-Diazodiphenylamine and Paraformaldehyde | 0.2 g |
| Polyvinyl Formal | 0.75 g |
| Compound No. 7 | 0.02 g |
| Crystal Violet | 0.02 g |
| Methyl Cellosolve | 20 g |
| Methanol | 5 g |

The application amount after drying was 0.98 g/m². This photosensitive lithographic printing plate was exposed to light for 30 seconds at a distance of 70 cm by a carbon arc lamp for 30 amperes. Since the exposed portions faded and the unexposed portions maintained their original density, print-out images the details of which could be discerned under a safety lamp were obtained.

Furhter, after dipping in the following developing solution for 1 minute at a room temperature, the surface was softly rubbed with absorbent cotton to remove the unexposed portions, by which a lithographic printing plate was obtained.

| | |
|---|---|
| Sodium Di-(2-ethylhexyl)phosphate | 10 g |
| Water | 90 g |

EXAMPLE 9

Process for Producing Negative Type Photosensitive Lithographic Printing Plate

The following photosensitive solution was applied to the aluminium plate (I) in the same manner as in Example 8 and dried.

| | |
|---|---|
| The p-Toluenesulfonate of the Condensation Product of p-Diazodiphenylamide and Paraformaldehyde | 0.2 g |
| Polyvinyl Formal | 0.75 g |
| Compound No. 7 | 0.02 g |
| N,N-Dimethylaniline | 0.02 g |
| Methyl Cellosolve | 20 g |
| Methanol | 5 g |

The application amount after drying was 1.0 g/m². When this photosensitive lithographic printing plate was subjected to imagewise exposure, print-out images the details of which could be discerned under a safety lamp were obtained, because the exposed portions colored violet and the unexposed portions maintained their original yellow color.

EXAMPLE 10

Process for Producing Negative Type Photosensitive Lithographic Printing Plate

The following photosensitive solution was applied to the aluminium plate (II) by the same manner as in Example 8 and dried.

| | | |
|---|---|---|
| Polyester Synthesized by the Condensation of Equimolor Amounts of Ethyl p-Phenylenediacrylate and 1,4-Bis-β-hydroxyethoxycyclohexane | 0.5 | g |
| 2-Benzoylmethylene-3-methyl-β-naphthothiazoline | 0.03 | g |
| Compound No. 7 | 0.008 | g |
| Leuco Crystal Violet | 0.008 | g |
| Monochlorobenzene | 9 | g |
| Ethylene Dichloride | 6 | g |

The application amount after drying was 1.2 g/m².

When this photosensitive lithographic printing plate was subjected to imagewise exposure, print-out images the details of which could be discerned under a safety lamp were obtained, because the exposed portions colored violet and the unexposed portions maintained their original yellow color.

EXAMPLE 11

Process for Producing Negative Type Photosensitive Lithographic Printing Plate

The following photosensitive solution was applied to the aluminium plate (II) in the same manner as in Example 8 and dried.

| | | |
|---|---|---|
| Esterified Product of Polyvinyl Alcohol (saponification value: 88%, degree of polymerization: 1000) and p-Azidobenzoic Acid | 0.5 | g |
| 1-Nitro-4-acetaminonaphthalene | 0.02 | g |
| Compound No. 3 | 0.008 | g |
| Leuco Crystal Violet | 0.008 | g |
| Dioctyl Phthalate | 0.1 | g |
| Ethylene Dichloride | 6 | g |
| Monochlorobenzene | 9 | g |

When this photosensitive lithographic printing plate was subjected to imagewise exposure, print-out images having high contrast were obtained.

EXAMPLE 12

Process for Producing Negative Type Photosensitive Lithographic Printing Plate

The following photosensitive solution was applied to the aluminium plate (II) and dried in the same manner as in Example 8.

| | | |
|---|---|---|
| Copolymer of Methacrylate and Methacrylic Acid (molor ratio of) copolymerization: 9:1) | 0.62 | g |
| Trimethylolpropane Triacrylate | 0.38 | g |
| Compound No. 7 | 0.02 | g |
| Leuco Crystal Violet | 0.008 | g |
| Methyl Ethyl Ketone | 10 | g |

When this photosensitive lithographic printing plate was subjected to imagewise exposure, print-out images having high contrast were obtained.

Then, a lithographic printing plate was obtained by removing the unexposed portions using a developing solution of 1.2 g of caustic soda, 300 ml of isopropyl alcohol and 900 ml of water.

While the invention has been described in detail and with reference to specific embodiments thereof, it will be apparent to one skilled in the art that various changes and modifications can be made therein without departing from the spirit and scope thereof.

What is claimed is:

1. In a photosensitive composition containing (1) a phosensitive compound selected from the group consisting of a photosensitive diazo compound, a photosensitive azide compound, an ethylenically unsaturated compound, and a compound which catalytically reacts with acids formed upon exposure to light and (2) a free radical generating agent, the improvement which comprises, said free radical generating agent being a 2-halomethyl-5-vinyl-1,3,4-oxadiazole compound represented by the following general formula (I):

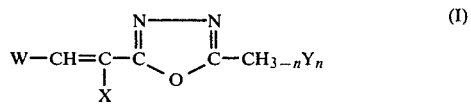

wherein W represents a substituted or unsubstituted aryl group, X represents a hydrogen atom, an alkyl group or an aryl group, Y represents a fluorine atom, a chlorine atom or a bromine atom, and n represents an integer of 1 to 3.

2. The photosensitive composition of claim 1, wherein said photosensitive composition additionally contains (3) a color changing agent which produces a color change under the influence of the light decomposition products of said free radical generating agent (2).

3. The photosensitive composition of claim 2, wherein said color changing agent (3) is a compound which is colorless and changes to a colored state upon exposure to light in the presence of said free radical generating agent (2) or is a compound which is colored and which discolors or fades upon exposure to light in the presence of said free radical generating agent (2).

4. The photosensitive composition of claim 1, wherein said photosensitive compound (1) is selected from the group consisting of a naphthoquinone diazide compound, a polyester containing a

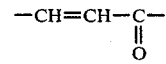

group, and a vinyl monomer containing at least 2 terminal vinyl groups.

5. The photosensitive composition of claim 2, wherein said color changing agent (3) is selected from the group consisting of a triphenylmethane type dye, an azine type dye, an anthraquinone type dye, and a leuco triphenylmethane type dye.

6. The photosensitive composition of claim 1, wherein said free radical generating agent (2) is present in an amount of 0.01 to 100 parts by weight per 100 parts by weight of said photosensitive compound (1).

7. The photosensitive composition of claim 4, wherein said photosensitive composition additionally contains (3) a color changing agent which produces a color change under the influence of the light decomposition products of said free radical generating agent (2).

8. The photosensitive composition of claim 7, wherein said color changing agent (3) is a compound which is colorless and changes to a colored state upon exposure to light in the presence of a free radical generating agent or is a compound which is colored and which discolors or fades upon exposure to light in the presence of said free radical generating agent (2).

9. The photosensitive composition of claim 8, wherein said color changing agent (3) is selected from the group consisting of a triphenylmethane type dye, an azine type dye, an anthraquinone type dye, and a leuco triphenylmethane type dye.

10. The photosensitive composition of claim 8, wherein said free radical generating agent (2) is present in an amount of 0.01 to 100 parts by weight and said color changing agent (3) is present in an amount of 0.1 to 50 parts by weight, each based on 100 parts by weight of said photosensitive compound (1).

11. The photosensitive composition of claim 8, wherein said free radical generating agent (2) is present in an amount of 0.1 to 50 parts by weight and said color changing agent (3) is present in an amount of 1 to 10 parts by weight, each based on 100 parts by weight of said photosensitive compound (1).

12. The photosensitive composition of claim 8, wherein said free radical generating agent (2) is a compound represented by the following general formula (I)

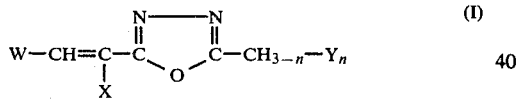

wherein W represents a phenyl group, an alkoxyphenyl group in which the alkoxy group has 1 to 6 carbon atoms, or a halophenyl group, X represents a hydrogen atom, Y represents a chlorine atom or a bromine atom, and n represents 3.

13. The photosensitive composition of claim 12, wherein said free radical generating agent (2) is

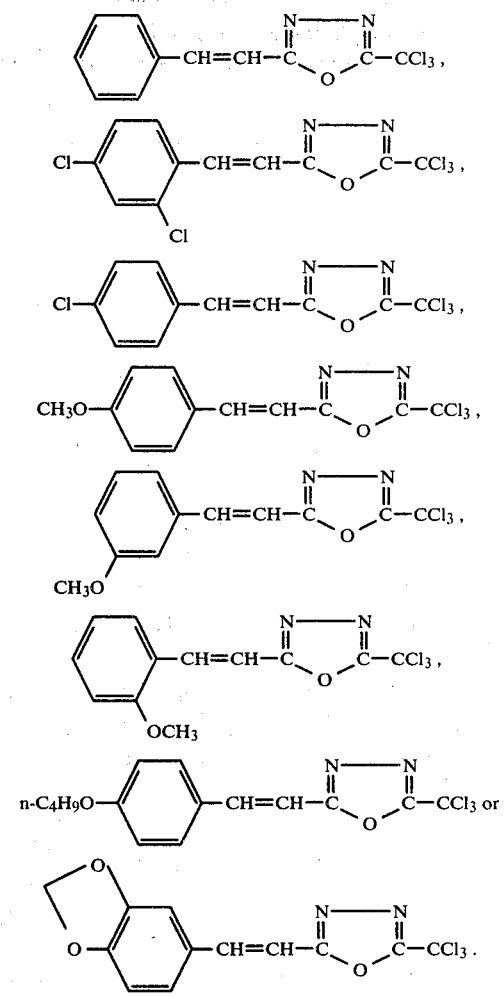

* * * * *